(12) United States Patent
U'Ren

(10) Patent No.: US 10,222,373 B2
(45) Date of Patent: *Mar. 5, 2019

(54) METHOD TO IDENTIFY ANTIGEN-SPECIFIC IMMUNE CELLS

(71) Applicant: RareCyte, Inc., Seattle, WA (US)

(72) Inventor: Lance U'Ren, Seattle, WA (US)

(73) Assignee: RareCyte, Inc., Seattle, WA (US)

( * ) Notice: Subject to any disclaimer, the term of this patent is extended or adjusted under 35 U.S.C. 154(b) by 100 days.

This patent is subject to a terminal disclaimer.

(21) Appl. No.: 15/228,466

(22) Filed: Aug. 4, 2016

(65) Prior Publication Data

US 2017/0248600 A1     Aug. 31, 2017

Related U.S. Application Data

(63) Continuation-in-part of application No. 15/185,577, filed on Jun. 17, 2016, now Pat. No. 9,442,113, which is a continuation-in-part of application No. 15/056,809, filed on Feb. 29, 2016, now Pat. No. 9,395,367.

(51) Int. Cl.
| | |
|---|---|
| *A61K 38/00* | (2006.01) |
| *C12N 5/00* | (2006.01) |
| *C12N 5/10* | (2006.01) |
| *G01N 33/68* | (2006.01) |
| *G01N 33/569* | (2006.01) |
| *G01N 33/566* | (2006.01) |
| *G01N 33/58* | (2006.01) |

(52) U.S. Cl.
CPC ..... *G01N 33/56972* (2013.01); *G01N 33/566* (2013.01); *G01N 33/56966* (2013.01); *G01N 33/582* (2013.01); *G01N 2333/70503* (2013.01)

(58) Field of Classification Search
None
See application file for complete search history.

(56) References Cited

U.S. PATENT DOCUMENTS

| | | |
|---|---|---|
| 5,326,696 A | 7/1994 | Chang |
| 5,627,052 A | 5/1997 | Schrader |
| 6,541,225 B1 | 4/2003 | Li |
| 8,945,857 B2 | 2/2015 | Schrader |
| 2004/0219611 A1 | 11/2004 | Racher |
| 2006/0148012 A1 | 7/2006 | Brown et al. |
| 2014/0248640 A1 | 9/2014 | Warren et al. |
| 2015/0104441 A1 | 4/2015 | Olweus et al. |

OTHER PUBLICATIONS

C. Langsdorf et al., Illuminating Endocytosis with Targeted pH-sensitive Fluorescent Compounds, ASCB 2013 Poster B1994, Life Technologies.

*Primary Examiner* — Michail A Belyavskyi
(74) *Attorney, Agent, or Firm* — Shay Glenn LLP

(57) ABSTRACT

This disclosure is directed to methods for retrieving and using at least one lymphocyte. Additionally, cell receptor sequences identified with this strategy could be used for antibody development, TCR discovery, or appropriate therapeutics development or evaluation.

15 Claims, 1 Drawing Sheet

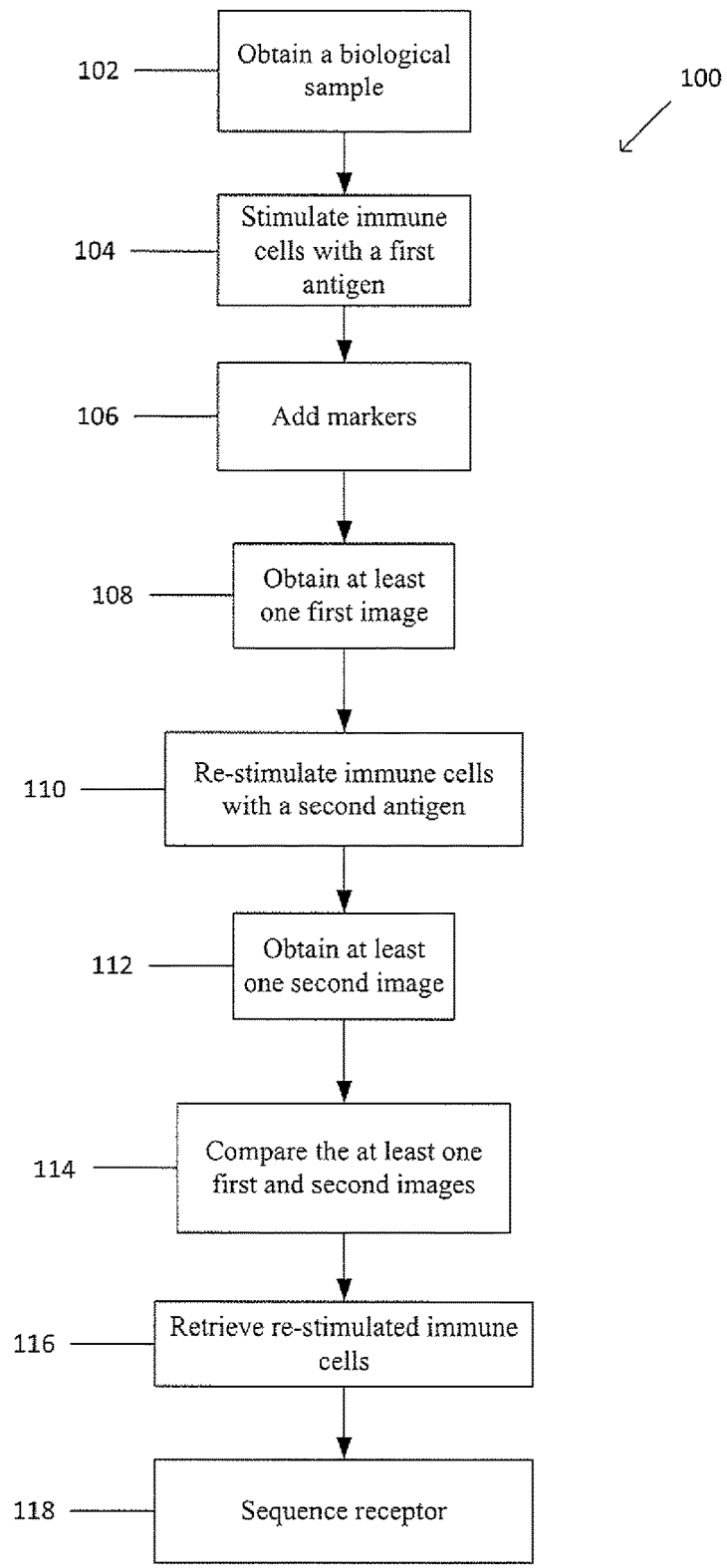

METHOD TO IDENTIFY ANTIGEN-SPECIFIC IMMUNE CELLS

CROSS-REFERENCE TO A RELATED APPLICATION

This application is a continuation-in-part of application Ser. No. 15/185,577, filed Jun. 17, 2016 (now U.S. Pat. No. 9,442,113, issued Sep. 13, 2016), which is a continuation-in-part of application Ser. No. 15/056,809, filed Feb. 29, 2016 (now U.S. Pat. No. 9,395,367, issued Jul. 19, 2016).

TECHNICAL FIELD

This disclosure relates generally to retrieving lymphocytes, such as B cells, T cells, and plasma cells and in particular, to retrieving and sequencing antigen-specific lymphocytes.

BACKGROUND

T cells and B cells express specialized receptors which can recognize and respond to very specific protein or peptide sequences, called T Cell Receptors (TCRs) and B Cell Receptors (BCRs) respectively. The activation of lymphocytes is an essential physiological response to fight off infections. Determining an individual's naïve and/or memory B or T cell count, such that the cells are specific for a particular antigen or peptide, may aid in determining the individual's response to a given therapy contain said antigen. Alternatively, an individual's precursor count may aid in predicting the individual's response to a given antigen or peptide, as would be the case with a vaccine. Furthermore, it may be desirous to be able to interrogate the native BCR repertoire to generate a fully human monoclonal antibody from the BCR sequence.

DESCRIPTION OF THE DRAWINGS

FIG. 1 shows an example method for retrieving and using immune cells.

DETAILED DESCRIPTION

This disclosure is directed to methods for retrieving and using at least one lymphocyte. Additionally, immune cell receptor sequences identified with this strategy could be used for antibody development, TCR discovery, or appropriate therapeutics development or evaluation.

For the sake of convenience, the method below is described with reference to at least one immune cell, such as a lymphocyte (i.e. B and/or T cells). But the method described below is not intended to be so limited in its scope of application and may be used for plasma cells, naïve B cells, memory B cells, naïve T cells, or memory T cells. The method may also be used with another appropriate biological analyte. Additionally, the method may be used for any number of cells or analytes, such as one, at least one, a plurality, etc.

Additionally, for the sake of convenience, the methods are described with reference to a sample of blood. But the methods described below are not intended to be so limited in their scope of application. The methods, in practice, may be used with any kind of suspension, solution, or fluid. For example, a sample may be urine, blood, buffy coat, red blood cells, plasma, bone marrow, cystic fluid, ascites fluid, stool, semen, cerebrospinal fluid, nipple aspirate fluid, saliva, amniotic fluid, vaginal secretions, mucus membrane secretions, aqueous humor, vitreous humor, vomit, lymphoid tissue suspension, tumor tissue, tumor digest, at least a portion of a tumor, at least one lymph node, and any other physiological fluid or semi-solid. The method may also be used with another appropriate solution or suspension.

For the sake of convenience, the methods below may label for and/or detect activation events (including, but not limited to, upregulation of an activation marker, such as CD69, CD154, CD137, or the like; BCR or TCR clustering; synapse formation between, for example, a lymphocyte and a tumor cell; cytokine production; or any other appropriate occurrence by which the immune cell, such as the lymphocyte, is activated upon recognizing the proper antigen). Furthermore, the images discussed in the methods below may include, but are not limited to, pictures, dot plots, scatter plots, histograms, or the like.

In the following description, the term "antigen" is used to describe a molecule capable of inducing an immune response. The antigen may include, but is not limited to a protein, including a protein which is expressed on the surface of a cell, a peptide, including a cell, such as an antigen-presenting cell, which presents the peptide, such as by a major histocompatibility complex, a virus, a tumor, a bacterium, a yeast, a protein complex, or the like. The "antigen" may also be a tumor cell or tissue, a portion of a tumor cell or tissue, or a component of a tumor cell or tissue. For example, to stimulate/re-stimulate the immune cells against a tumor antigen, the immune cells may be incubated with a tumor cell (which expresses a given protein or peptide on the surface) or a tumor cell lysate, including a membrane fraction of a tumor cell lysate.

The methods of retrieving a lymphocyte and developing a therapeutic include, generally, the following steps. First, a sample suspected of containing at least one immune cell comprising at least one receptor is collected. The sample may be obtained by venipuncture or by any appropriate method of sample collection, including enrichment and/or isolation. The biological sample may be enriched by any appropriate enrichment process including, but not limited to, sequential density fractionation, magnetic-activated cell sorting, fluorescence-activated cell sorting, differential lysis, depletion filters, microfluidic device separation, or the like. Sequential density fractionation is a process by which a sample is divided into fractions or a fraction of a sample is divided into sub-fractions by a step-wise or sequential process, such that each step or sequence results in the collection or separation of a different fraction or sub-fraction from the preceding and successive steps or sequences. In other words, sequential density fractionation provides individual sub-populations of a population or individual sub-sub-populations of a sub-population of a population through a series of steps. For example, separation fluids may be used whereby each separation fluid has a different density, thereby separating a fraction of a sample into sub-fractions based on the densities of the respective sub-fractions via the different density separating fluids.

Next, the at least one immune cell (for example, B and/or T cell) is stimulated with a first aliquot of an antigen. Subsequently, any excess antigen of the first aliquot is washed away. The at least one immune cell may then be re-stimulated with a second aliquot of the antigen. The at least one immune cell that was re-stimulated is then retrieved, and the at least one receptor (for example, B Cell Receptor and/or T Cell Receptor) is sequenced. Alternatively, the at least one immune cell that was re-stimulated is then enumerated. Alternatively, the at least one immune cell that was re-stimulated is then imaged.

Alternatively, the at least one immune cell (for example, B and/or T cell) may have been stimulated an antigen in vivo, such as when the sample is a biological sample collected directly or indirectly from a patient or subject. Subsequently, any excess antigen may be washed away and/or the sample may be rested or cultured. The at least one immune cell may then be re-stimulated, such as ex vivo or in vitro, with a separate aliquot of the antigen that initially stimulated the at least one immune cell. The at least one immune cell that was re-stimulated is then retrieved, and the at least one receptor (for example, B Cell Receptor and/or T Cell Receptor) is sequenced. Alternatively, the at least one immune cell that was re-stimulated is then enumerated. Alternatively, the at least one immune cell that was re-stimulated is then imaged.

A receptor-dependent substance based on the sequence of the at least one receptor is then generated. The receptor-dependent substance may include, but is not limited to, a monoclonal antibody, a modified cell expressing the same or substantially the same B Cell Receptor as the retrieved immune cell, a soluble T Cell Receptor, or a modified cell expressing the same or substantially the same T Cell Receptor as the retrieved immune cell.

The steps of the methods described above may be performed by at least one of a fluorescent microscope, a flow cytometer, or a microfluidic device, such as a chip or a microchannel. For example, the flow cytometer may be used for the collecting step, where enrichment via fluorescent-activated cell sorting is appropriate, and the microfluidic device may be used for the retrieving step. In other words, the methods, though described below to include one device per method, may be performed such that a combination of devices is used.

Example Methods I

FIG. 1 shows a flow diagram of an example method 100 for retrieving and using immune cells. In block 102, a biological sample, such as blood, suspected of containing immune cells including receptors is obtained, such as by venipuncture. Alternatively, the biological sample may be a fraction of a suspension, such that the biological sample is obtained through enrichment, including positive and/or negative enrichment. The enriched fraction includes at least one immune cell. The biological sample may be enriched by any appropriate enrichment process including, but not limited to, sequential density fractionation, magnetic-activated cell sorting, fluorescence-activated cell sorting, differential lysis, depletion filters, microfluidic device separation, or the like. Sequential density fractionation is a process by which a sample is divided into fractions or a fraction of a sample is divided into sub-fractions by a step-wise or sequential process, such that each step or sequence results in the collection or separation of a different fraction or sub-fraction from the preceding and successive steps or sequences. In other words, sequential density fractionation provides individual sub-populations of a population or individual sub-sub-populations of a sub-population of a population through a series of steps. For example, separation fluids may be used whereby each separation fluid has a different density, thereby separating a fraction of a sample into sub-fractions based on the densities of the respective sub-fractions via the different density separating fluids.

In block 104, a first antigen is added to the biological sample to stimulate the immune cells, such as by re-distributing the receptors or by expressing activation markers. The receptors, for example, may be endocytosed. In addition to the re-distribution of the receptors, the antigen may cause co-localization of the receptors and at least one lysosome. The lysosome may also be labeled with a fluorescent probe, though with a different fluorescent molecule than the receptors. Alternatively, the receptors may undergo capping or be expelled.

After adding the first antigen, an excess of the first antigen may be washed away. The immune cells may then be incubated with the remaining first antigen. The incubation time may last any appropriate time, such as up to 720 hours, such as up to 24 hours, including, 1 hour, 2, hours, 4 hours, 12 hours, etc. The incubation may allow the receptors of the immune cells to return to the receptors' original location relative to the immune cells, such as on the outer surface of the immune cells. The sample may also be purified of the first antigen, when it is desirous to do so.

In block 106, fluorescent probes may be added to the sample to label the immune cells and/or the receptors (i.e. receptor probes). The fluorescent probes, for example, may be used to label the immune cells, thereby providing a fluorescent signal for identification and characterization. The fluorescent probe may include a fluorescent molecule bound to a ligand. Ligands can be used to highlight and classify the immune cells present in the suspension by conjugating ligands that attach to particular receptors or biomarkers with a particular fluorescent molecule. Additionally, the fluorescent probes may include activation markers to determine that the immune cells have been activated or stimulated. For example, the fluorescent molecules may include, but are not limited to pH-sensitive dyes, such as AcidiFluor, pHrodo® (ThermoFisher), CypHER5E (GE), 2',7'-bis(2-carboxyethyl)-5(6)-carboxyfluorescein tetrakis (acetoxymethyl) ester (BCECF AM), 5(6)-carboxy-2',7'-dichloro fluorescein, 5(6)-carboxyfluorescein, 5(6)-carboxyfluorescein diacetate, 5(6)-carboxyfluorescein N-hydroxysuccinimide ester, 3,6-diacetoxyphthalonitrile, 6,8-dihydroxy-1,3-pyrenedisulfonic acid disodium salt, Eosin diacetate, and naphthofluorescein; quantum dots; commercially available dyes, such as fluorescein, FITC ("fluorescein isothiocyanate"), R-phycoerythrin ("PE"), Texas Red, allophycocyanin, Cy5, Cy7, cascade blue, Hoechst, DAPI ("4',6-diamidino-2-phenylindole") and TRITC ("tetramethylrhodamine isothiocyanate"); combinations of dyes, such as CY5PE, CY7APC, and CY7PE; and synthesized molecules, such as self-assembling nucleic acid structures. The pH-sensitive dye may fluoresce in an acidic environment but not fluoresce in a basic environment. Alternatively, the pH-sensitive dye may fluoresce in a neutral or basic environment but not fluoresce in an acidic environment.

In block 108, a first image or first set of images (collectively, the "first images") are obtained by imaging. The first images may depict the immune cells having been activated or stimulated, though with receptors that have returned to the receptors' original location relative to the immune cells.

To image the immune cells, the sample is illuminated with one or more wavelengths of excitation light from a light source, such as red, blue, green, and ultraviolet. The imaging may be done with a flow cytometer or a microscope, such as a fluorescent microscope, a scanner, or the like. Imaging may be done in fluorescence, bright field, or dark field. The images formed from the emission light of each fluorescent molecule can be overlaid when a plurality of fluorescent molecules are excited and emit light. The images may then be analyzed to detect, locate, and characterize the immune cells. Imaging may be performed in a tube, on a microscope slide, or in any appropriate vessel or substrate for imaging.

The immune cells that were stimulated by the first antigen may be sorted or moved into a first bin, effectively being separated from the cells that were not stimulated by the first antigen.

In block 110, a second antigen is added to the biological sample to re-stimulate the immune cells, thereby re-distributing the receptors. The receptors, for example, may be endocytosed. In addition to the re-distribution of the receptors, the antigen may cause co-localization of the receptors and at least one lysosome. The lysosome may also be labeled with a fluorescent probe, though with a different fluorescent molecule than the receptors. Alternatively, the receptors may undergo capping or be expelled.

Alternatively, the first images may be obtained after adding the second antigen and before obtaining the second images, as the second antigen may not immediately cause re-distribution of the receptors. The first images may be obtained within a given time frame after adding the second antigen (i.e. up to 4 hours, including 30 minutes, 60 minutes, 90 minutes, and hours). For example, the first images may be obtained 5 minutes after adding the second antigen, then the sample may be allow to incubate with the second antigen to provide ample time to re-stimulate the immune cells. The second images may then be obtained.

Additional fluorescent probes may be added to the stimulated or re-stimulated immune cells to label the stimulated or re-stimulated immune cells and/or the receptors (i.e. receptor probes), when it is desirous to do so, such as when the fluorescent probes initially added are no longer functional (i.e. degraded) or no longer have the desired emission intensity. The fluorescent probe used may the same as or different than the fluorescent probe used in step 106 above.

In block 112, a second image or second set of images (collectively, the "second images") are obtained by imaging. The second images may depict the re-distributed receptors after re-stimulation in response to the second antigen. Optionally, a third image or third set of images (collectively, the "third images") are obtained by imaging after a pre-determined amount of time (i.e. up to 168 hours) has elapsed after obtaining the second images. Changes in mean fluorescent intensity of fluorescent probes between the second and third images may be calculated to determine antibody affinity.

In block 114, the first and second images are compared to dump and retain cells or analytes (i.e. determine that the receptors were re-distributed in response to the second antigen added during the re-stimulating step), such as by image analysis. Any cell or analyte from the second image(s) that appears identical or substantially similar to the first image(s) of the same cell or analyte may be dumped (i.e. where the receptors were not re-distributed in response to the second antigen). Any cell or analyte from the second image(s) that do not appear identical or substantially similar to the first image(s) taken of the same cell or analyte may be retained (i.e. where the receptors were re-distributed in response to the second antigen). For example, cells that endocytosed receptors in the first images are dumped (i.e. no longer considered or removed from consideration) as those cells may be the result of non-specific staining or were already activated prior to the addition of the first antigen. Additionally, co-localization of the immune cell receptor and at least one lysosome may be compared, when it is desirous to do so.

Alternatively, the stimulated immune cells that were re-stimulated by the second antigen may be sorted into a second bin, effectively being separated from the cells that were not re-stimulated by the second antigen.

In block 116, the immune cells are retrieved from the rest of the sample. To retrieve the immune cells, the immune cells may undergo enrichment and/or isolation. The immune cells may be enriched by any appropriate enrichment process including, but not limited to, sequential density fractionation, magnetic-activated cell sorting, fluorescence-activated cell sorting, differential lysis, depletion filters, microfluidic device separation, or the like. Sequential density fractionation is a process by which a sample is divided into fractions or a fraction of a sample is divided into sub-fractions by a step-wise or sequential process, such that each step or sequence results in the collection or separation of a different fraction or sub-fraction from the preceding and successive steps or sequences. In other words, sequential density fractionation provides individual sub-populations of a population or individual sub-sub-populations of a sub-population of a population through a series of steps. For example, separation fluids may be used whereby each separation fluid has a different density, thereby separating a fraction of a sample into sub-fractions based on the densities of the respective sub-fractions via the different density separating fluids. The immune cells may be isolated from rest of the sample, whether with or without prior enrichment, by selecting at least one immune cell at a time with any appropriate device or system for picking a cell. Imaging the sample or a portion thereof, as discussed above, may be performed to aid in isolation by providing location and characterization information for isolation purposes. Enrichment or isolation may also act to identify at least one immune cell, whether it is already-stimulated, unstimulated, or newly stimulated.

In block 118, the isolated immune cells undergo sequencing. The immune cell receptor on the immune cell may be analyzed and sequenced using any appropriate method or technique, though more specifically extracellular and intracellular analysis including intracellular protein labeling; nucleic acid analysis, including, but not limited to, DNA arrays, expression arrays, protein arrays, and DNA hybridization arrays; in situ hybridization ("ISH"—a tool for analyzing DNA and/or RNA, such as gene copy number changes); polymerase chain reaction ("PCR"); reverse transcription PCR; or branched DNA ("bDNA"—a tool for analyzing DNA and/or RNA, such as mRNA expression levels) analysis. Sequencing may be done on the entire genome, the transcriptome, or cDNA, which may be synthesized from mRNA, such as by reverse transcriptase.

Alternatively, additional information about the retrieved immune cell or cells may be collected. For example, the retrieved immune cell or cells may be enumerated. As another example, the retrieved immune cell or cells may be used to generate or be analyzed by an assay, such as for evaluating or determining therapeutics, target molecules, or the like. The collection of the additional information may be performed before or after the sequencing or instead of the sequencing and generating steps.

After properly sequencing the receptors, the receptor sequence may then be used to develop antibodies against respective antigens, such as for fully human monoclonal antibody production, to create, a modified cell expressing the same or substantially the same B Cell Receptor as the retrieved immune cell, to create soluble immune cell receptors, or to create modified cells which express the immune cell receptor of the retrieved immune cell. Alternatively, the screening step may be used to identify patients who may have adverse reactions (i.e. autoimmune response) to the suggested therapies or to identify patients who are more likely to respond to a therapy (i.e. vaccination).

The methods can be modified for use as a T cell receptor (TCR) discovery platform by similarly following the endocytosis of TCRs or presence of activation markers due to peptide, antigen-presenting cell, or protein (re-)stimulation and comparing against the pre-stimulation and/or post-stimulation images, where appropriate.

1. Collect sample (blood, bone marrow, or tissue)
2. (Optional) Isolate target material (buffy coat or tissue digest)
3. (Optional) Immune cell enrichment
   a. Magnetic or bead/weight separation
   b. Fluorescent activated cell sorting (FACS)
   c. Rosetting non-target cells with tetrameric antibodies
   d. Sequential density fractionation (SDF)
   e. Microfluidic Device
4. Stimulate immune cells with first antigen
   a. Add first antigen
5. (Optional) Wash away excess first antigen
6. (Optional) Incubate immune cells with first antigen
7. Add antibody cocktail for labeling
   a. Add activation markers to label immune cells
   b. Add receptor probes to label immune cell receptors
   c. Add additional antibody-dye complexes to confirm or characterize immune cells
      i. CD19, CD20, maturation markers
      ii. BCR isotype (IgG1, IgG2a, IgG2b, IgM, IgA)
      iii. Nuclear (DAPI, Cytox Orange, Syto 9)
      iv. Exclusion markers (CD14, CD66b, CD15, CD3, dead cell indicator)
8. Incubate antibody cocktail
   a. 0-45° C.
   b. Up to approximately 24 hours (e.g. 1 hour)
9. Place labeled cells on substrate for imaging and/or archiving
10. Obtain First Image(s)
11. Adding a second antigen to re-stimulate immune cells with
    a. The second antigen may be identical to the first antigen
    b. Alternatively, the second antigen may be substantially similar, though not identical to, the first antigen
12. Obtain Second Image(s)
13. (Optional) Obtain Third Image(s) after a given amount of time has elapsed after obtaining the Second Image(s)
    a. Determine change(s) in mean fluorescent intensity of markers Second and Third Images
    b. Determine antibody affinity based on change(s) in mean fluorescent intensity
14. Compare First and Second Image(s) to retain and dump cells or analytes, such as by image analysis
    a. Dump any cell or analyte from the Second Image(s) that appears identical or substantially similar to the First Image(s) of the same cell or analyte
       i. For example, where the receptors were not re-distributed in response to the second antigen
    b. Retain cell or analyte from the Second Image(s) that do not appear identical or substantially similar to the First Image(s) taken of the same cell or analyte
       i. For example, where the receptors were re-distributed in response to the second antigen
15. (Optional) Enumerate retained immune cell(s)
16. Retrieve retained immune cell(s)
17. Obtain RNA or DNA
18. Sequence the receptors or obtain other information from RNA/DNA
    a. RNAseq, RT-PCT, or the like
    b. Entire genome
    c. Transcriptome
    d. cDNA
       i. Synthesize cDNA from mRNA
          1. Using reverse transcriptase
19. Use receptor sequence to generate receptor-dependent substance
    a. Monoclonal antibody
       i. Fully human antibody
       ii. Fully Animal-derived antibody
          1. Rabbit
          2. Goat
          3. Mouse
          4. Rat
    b. Modified cell expressing the same or substantially the same B Cell Receptor as the retrieved immune cell
    c. Soluble T Cell Receptor
    d. Modified cell expressing the same of substantially the same T Cell Receptor as the retrieved immune cell
1. Collect sample (blood, bone marrow, or tissue)
2. (Optional) Isolate target material (buffy coat or tissue digest)
3. (Optional) Immune cell enrichment
   a. Magnetic or bead/weight separation
   b. Fluorescent activated cell sorting (FACS)
   c. Rosetting non-target cells with tetrameric antibodies
   d. Sequential density fractionation (SDF)
   e. Microfluidic Device
4. Stimulate immune cells with first antigen
   a. Add first antigen
5. (Optional) Wash away excess first antigen
6. (Optional) Incubate immune cells with first antigen
7. Add antibody cocktail for labeling
   a. Label activation markers
   b. Add receptor probes to label immune cell receptors
   c. Add additional antibody-dye complexes to confirm or characterize immune cells
      i. CD19, CD20, maturation markers
      ii. BCR isotype (IgG1, IgG2a, IgG2b, IgM, IgA)
      iii. Nuclear (DAFT, Cytox Orange, Syto 9)
      iv. Exclusion markers (CD14, CD66b, CD15, CD3, dead cell indicator)
8. Incubate antibody cocktail
   a. 0-45° C.
   b. Up to approximately 24 hours (e.g. 1 hour)
9. Process cells through flow cytometer
   a. Obtain First Image(s)
   b. Retain stimulated immune cells in first bin
10. Adding a second antigen to re-stimulate immune cells from the first bin
    a. The second antigen may be identical to the first antigen
    b. Alternatively, the second antigen may be substantially similar, though not identical to, the first antigen
11. (Optional) Add antibody cocktail for labeling
    a. May be same or different label than above
12. Re-process cells through flow cytometer
    a. Obtain Second Image(s)
    b. Retain re-stimulated immune cells in second bin
13. (Optional) Obtain Third Image(s) after a given amount of time has elapsed after obtaining the Second Image(s)

a. Determine change(s) in mean fluorescent intensity of markers Second and Third Images
  b. Determine antibody affinity based on change(s) in mean fluorescent intensity
14. Retrieve retained immune cells
15. Obtain RNA or DNA
16. Sequence the receptors or obtain other information from RNA/DNA
  a. RNAseq, RT-PCT, or the like
  b. Entire genome
  c. Transcriptome
  d. cDNA
    i. Synthesize cDNA from mRNA
      1. Using reverse transcriptase
17. Use receptor sequence to generate receptor-dependent substance
  a. Monoclonal antibody
    i. Fully human antibody
    ii. Fully Animal-derived antibody
      1. Rabbit
      2. Goat
      3. Mouse
      4. Rat
  b. Modified cell expressing the same or substantially the same B Cell Receptor as the retrieved immune cell
  c. Soluble T Cell Receptor
  d. Modified cell expressing the same of substantially the same T Cell Receptor as the retrieved immune cell
1. Collect sample (blood, bone marrow, or tissue)
2. (Optional) Isolate target material (buffy coat or tissue digest)
3. (Optional) Immune cell enrichment
  a. Magnetic or bead/weight separation
  b. Fluorescent activated cell sorting (FACS)
  c. Rosetting non-target cells with tetrameric antibodies
  d. Sequential density fractionation (SDF)
  e. Microfluidic Device
4. Stimulate immune cells with first antigen
  a. Add first antigen
5. (Optional) Wash away excess first antigen
6. (Optional) Incubate immune cells with first antigen
7. Add antibody cocktail for labeling
  a. Add activation markers to label immune cells
  b. Add receptor probes to label immune cell receptors
  c. Add additional antibody-dye complexes to confirm or characterize immune cells
    i. CD19, CD20, maturation markers
    ii. BCR isotype (IgG1, IgG2a, IgG2b, IgM, IgA)
    iii. Nuclear (DAPI, Cytox Orange, Syto 9)
    iv. Exclusion markers (CD14, CD66b, CD15, CD3, dead cell indicator)
8. Incubate antibody cocktail
  a. 0-45° C.
  b. Up to approximately 24 hours (e.g. 1 hour)
9. Process cells with a microfluidic device
  a. Obtain First Image(s)
  b. Retain stimulated immune cells in first bin
10. Adding a second antigen to re-stimulate immune cells from the first bin
  a. The second antigen may be identical to the first antigen
  b. Alternatively, the second antigen may be substantially similar, though not identical to, the first antigen
11. (Optional) Add antibody cocktail for labeling
  a. May be same or different label than above
12. Re-process cells with the microfluidic device
  a. Obtain Second Image(s)
  b. Retain re-stimulated immune cells in second bin
13. (Optional) Obtain Third Image(s) after a given amount of time has elapsed after obtaining the Second Image(s)
  a. Determine change(s) in mean fluorescent intensity of markers Second and Third Images
  b. Determine antibody affinity based on change(s) in mean fluorescent intensity
14. Retrieve retained immune cells
15. Obtain RNA or DNA
16. Sequence the receptors or obtain other information from RNA/DNA
  a. RNAseq, RT-PCT, or the like
  b. Entire genome
  c. Transcriptome
  d. cDNA
    i. Synthesize cDNA from mRNA
      1. Using reverse transcriptase
17. Use receptor sequence to generate receptor-dependent substance
  a. Monoclonal antibody
    i. Fully human antibody
    ii. Fully Animal-derived antibody
      1. Rabbit
      2. Goat
      3. Mouse
      4. Rat
  b. Modified cell expressing the same or substantially the same B Cell Receptor as the retrieved immune cell
  c. Soluble T Cell Receptor
  d. Modified cell expressing the same of substantially the same T Cell Receptor as the retrieved immune cell Example Methods II Alternatively, a method may be implemented where an immune cell has been stimulated prior to collection, such as in vivo stimulation. That method includes the steps of:
1. Collect sample (blood, bone marrow, or tissue)
2. (Optional) Isolate target material (buffy coat or tissue digest)
3. Enrich already-stimulated immune cells
  a. Magnetic or bead/weight separation
  b. Fluorescent activated cell sorting (FACS)
  c. Rosetting non-target cells with tetrameric antibodies
  d. Sequential density fractionation (SDF)
  e. Microfluidic Device
4. Add antibody cocktail for labeling
  a. Add activation markers to label immune cells
  b. Add receptor probes to label immune cell receptors
  c. Add additional antibody-dye complexes to confirm or characterize immune cells
    i. CD19, CD20, maturation markers
    ii. BCR isotype (IgG1, IgG2a, IgG2b, IgM, IgA)
    iii. Nuclear (DAPI, Cytox Orange, Syto 9)
    iv. Exclusion markers (CD14, CD66b, CD15, CD3, dead cell indicator)
5. Incubate antibody cocktail
  a. 0-45° C.
  b. Up to approximately 24 hours (e.g. 1 hour)
6. Process cells with an imaging device (microscope, flow cytometer, or microfluidic device)
  a. Obtain First Image(s)
  b. Retain stimulated immune cells, where appropriate 7. Rest or culture the enriched, already-stimulated immune cells
    a. Rest/culture step may last up to 720 hours
8. Add an antigen to re-stimulate immune cells that is identical or substantially similar to the antigen that initially stimulated the immune cells
9. (Optional) Add antibody cocktail for labeling
    a. May be same or different label than above
10. Re-process cells with the imaging device (microscope, flow cytometer, or microfluidic device)
    a. Obtain Second Image(s)
    b. Retain re-stimulated immune cells, where appropriate
11. (Optional) Obtain Third Image(s) after a given amount of time has elapsed after obtaining the Second Image(s)
    a. Determine change(s) in mean fluorescent intensity of markers Second and Third Images
    b. Determine antibody affinity based on change(s) in mean fluorescent intensity
12. Retrieve re-stimulated immune cells
13. Obtain RNA or DNA
14. Sequence the receptors or obtain other information from RNA/DNA
    a. RNAseq, RT-PCT, or the like
    b. Entire genome
    c. Transcriptome
    d. cDNA
        i. Synthesize cDNA from mRNA
            1. Using reverse transcriptase
15. Use receptor sequence to generate receptor-dependent substance
    a. Monoclonal antibody
        i. Fully human antibody
        ii. Fully Animal-derived antibody
            1. Rabbit
            2. Goat
            3. Mouse
            4. Rat
    b. Modified cell expressing the same or substantially the same B Cell Receptor as the retrieved immune cell
    c. Soluble T Cell Receptor
    d. Modified cell expressing the same of substantially the same T Cell Receptor as the retrieved immune cell The steps of the method described above may be performed by at least one of a fluorescent microscope, a flow cytometer, or a microfluidic device, such as a chip or a microchannel. For example, the flow cytometer may be used for the collecting step, where enrichment via fluorescent-activated cell sorting is appropriate, and the microfluidic device may be used for the retrieving step. In other words, the methods, though described below to include one device per method, may be performed such that a combination of devices is used.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments are presented by way of examples for purposes of illustration and description. They are not intended to be exhaustive of or to limit this disclosure to the precise forms described. Many modifications and variations are possible in view of the above teachings. The embodiments are shown and described in order to best explain the principles of this disclosure and practical applications, to thereby enable others skilled in the art to best utilize this disclosure and various embodiments with various modifications as are suited to the particular use contemplated. It is intended that the scope of this disclosure be defined by the following claims and their equivalents:

I claim:

1. A method comprising:
    collecting a sample suspected of containing at least one immune cell;
    re-stimulating the at least one immune cell with an aliquot of an antigen, the at least one immune cell having been stimulated with the antigen prior to at least the re-stimulating step; and
    retrieving the at least one immune cell that was re-stimulated during the re-stimulating step.

2. The method of claim 1, further comprising:
    stimulating the at least one immune cell with a separate aliquot of the antigen; and
    washing away any excess antigen of the separate aliquot,
    wherein the stimulating and washing steps are performed before the re-stimulating step.

3. The method of claim 2, further comprising the step of incubating the at least one immune cell with the separate aliquot of the antigen.

4. The method of claim 3, wherein the incubation step is performed after the washing step.

5. The method of claim 1, further comprising:
    stimulating the at least one immune cell with a separate aliquot of the antigen; and
    resting the at least one immune cell,
    wherein the stimulating step is performed in vivo and before the collecting step,
    wherein the resting step is performed after the collecting step, and
    wherein the re-stimulating is performed in vitro or ex vivo.

6. The method of claim 1, further comprising the step of labeling the at least one immune cell with at least one fluorescent probe comprising a fluorescent molecule bound to a ligand which is bound to a biomarker on the at least one immune cell.

7. The method of claim 6, wherein the labeling step occurs after the re-stimulating step.

8. The method of claim 6, further comprising the step of obtaining at least one image of the at least one immune cell.

9. The method of claim 8, wherein the obtaining step occurs after the labeling step and before the re-stimulating step.

10. The method of claim 6, further comprising the step of obtaining at least one image to determine that the at least one immune cell was re-stimulated in response to the separate aliquot of the antigen.

11. The method of claim 10, wherein the obtaining step occurs after the labeling and re-stimulating steps.

12. The method of claim 1, further comprising the step of enumerating the at least one immune cell that was re-stimulated during the re-stimulating step.

13. The method of claim 1, further comprising the step of generating an assay based on the at least one immune cell that was re-stimulated during the re-stimulating step.

14. The method of claim 1, further comprising the step of analyzing the at least one immune cell that was re-stimulated during the re-stimulating step with an assay.

15. The method of claim 1, wherein the immune cell is a B cell or a T cell.

* * * * *